(12) United States Patent
Van Achthoven et al.

(10) Patent No.: US 11,071,835 B2
(45) Date of Patent: Jul. 27, 2021

(54) INHALABLE MEDICAMENTS

(71) Applicant: PHARMACHEMIE B.V., GA Haarlem (NL)

(72) Inventors: Erwin Van Achthoven, GA Haarlem (NL); Johan Keegstra, GA Haarlem (NL); Michael Imre Goller, GA Haarlem (NL)

(73) Assignee: PHARMACHEMIE B.V., Haarlem (NL)

( * ) Notice: Subject to any disclaimer, the term of this patent is extended or adjusted under 35 U.S.C. 154(b) by 1197 days.

(21) Appl. No.: 15/101,718

(22) PCT Filed: Nov. 19, 2014

(86) PCT No.: PCT/EP2014/075058
§ 371 (c)(1),
(2) Date: Jun. 3, 2016

(87) PCT Pub. No.: WO2015/086278
PCT Pub. Date: Jun. 18, 2015

(65) Prior Publication Data
US 2016/0303337 A1    Oct. 20, 2016

(30) Foreign Application Priority Data

Dec. 9, 2013  (GB) ..................................... 1321717

(51) Int. Cl.
*A61M 15/00*  (2006.01)
*A61K 9/00*  (2006.01)
(Continued)

(52) U.S. Cl.
CPC ....... *A61M 15/0008* (2014.02); *A61K 9/0075* (2013.01); *A61K 9/145* (2013.01);
(Continued)

(58) Field of Classification Search
CPC . A61M 15/0005–0008; A61M 15/0091–0096; A61M 15/0065; A61M 2202/064; A61K 9/0075
See application file for complete search history.

(56) References Cited

U.S. PATENT DOCUMENTS 6,718,972 B2* 4/2004 O'Leary ........... A61M 15/0045
                                                  128/203.12
7,759,328 B2  7/2010 Govind et al.
(Continued)

FOREIGN PATENT DOCUMENTS

EP    1486227 A2   12/2004
EP    2682108      1/2014
(Continued)

OTHER PUBLICATIONS

OGD FY13-FY17 Regulatory Science Research Report; FYs 2013-2017 Regulatory Science Report: Locally-Acting Orally Inhaled and Nasal Drug Products; 13 pages.
(Continued)

*Primary Examiner* — Valerie L Woodward
(74) *Attorney, Agent, or Firm* — BakerHostetler

(57) ABSTRACT

Described herein is a dry powder inhaler which includes: a reservoir containing a dry powder formulation and an arrangement for delivering a metered dose of the medicament from the reservoir; a cyclone deagglomerator for breaking up agglomerates of the dry powder medicament; a delivery passageway for directing an inhalation-induced air flow through a mouthpiece, the delivery passageway extending to the metered dose of medicament, and an inhalable β2-agonist having a particle size distribution of d10<1 μm, d50=1-3 μm, d90=3.5-6 μm and NLT 99% 10 μm and a lactose carrier.

15 Claims, 15 Drawing Sheets

(51) Int. Cl.
*A61K 31/167* (2006.01)
*A61K 31/58* (2006.01)
*A61K 31/137* (2006.01)
*A61K 31/4704* (2006.01)
*A61K 31/24* (2006.01)
*A61K 45/06* (2006.01)
*A61K 31/44* (2006.01)
*A61K 31/15* (2006.01)
*A61K 9/14* (2006.01)
*A61K 31/165* (2006.01)

(52) U.S. Cl.
CPC .......... *A61K 31/137* (2013.01); *A61K 31/165* (2013.01); *A61K 31/167* (2013.01); *A61K 31/24* (2013.01); *A61K 31/44* (2013.01); *A61K 31/4704* (2013.01); *A61K 31/58* (2013.01); *A61K 45/06* (2013.01); *A61M 15/009* (2013.01); *A61M 15/0021* (2014.02); *A61M 15/0028* (2013.01); *A61M 15/0078* (2014.02); *A61M 15/0086* (2013.01); *A61M 15/0091* (2013.01); *A61M 15/0026* (2014.02); *A61M 2202/064* (2013.01); *A61M 2206/16* (2013.01); *A61M 2206/20* (2013.01)

(56) References Cited

U.S. PATENT DOCUMENTS

| | | |
|---|---|---|
| 7,897,646 B2 | 3/2011 | Bauer et al. |
| 8,143,239 B2 | 3/2012 | Govind et al. |
| 8,461,211 B2 | 6/2013 | Bauer et al. |
| 8,575,137 B2 | 11/2013 | Govind et al. |
| 9,402,825 B2 * | 8/2016 | Pasquali .................. A61P 11/08 |
| 10,387,621 B2 * | 8/2019 | McNair ................ A61M 11/005 |
| 2001/0002461 A1 * | 9/2001 | Yang .................... A61K 47/183 424/46 |
| 2002/0078950 A1 | 6/2002 | O'Leary |
| 2002/0088463 A1 | 7/2002 | Keane |
| 2011/0192397 A1 * | 8/2011 | Saskar ............. A61M 15/0045 128/200.17 |
| 2011/0308519 A1 * | 12/2011 | Schiaretti ........... A61K 9/0075 128/203.15 |
| 2012/0031403 A1 * | 2/2012 | Cocconi ............. A61K 9/0075 128/203.15 |
| 2013/0037024 A1 * | 2/2013 | Muellinger ............ A61M 11/06 128/203.12 |
| 2013/0319411 A1 * | 12/2013 | Weers ................. A61K 9/0075 128/203.15 |

FOREIGN PATENT DOCUMENTS

| | | |
|---|---|---|
| WO | 2001/097889 | 12/2001 |
| WO | WO 2002/00281 | 1/2002 |
| WO | 2007/077162 | 7/2007 |
| WO | 2009/010770 | 1/2009 |
| WO | 2009/158300 A1 | 12/2009 |
| WO | WO 2010/138862 | 12/2010 |
| WO | WO 2011/093817 | 8/2011 |
| WO | 2012/174327 A1 | 12/2012 |

OTHER PUBLICATIONS

New Pharmacy, Ewha Womans University Press, vol. 3, 2004, pp. 500-501 (Cited in Korean Office Action dated Jun 24, 2020, English translation attached indicates relevancy of Non-Patent Literature Document).

Pharmaceutical Dosage Forms, Pharmaceutical Sciences Series 1, Shinil Books, 2009, pp. 148-149; (Cited in Korean Office Action dated Jun 24, 2020, English translation attached indicates relevancy of Non-Patent Literature Document).

* cited by examiner

INHALABLE MEDICAMENTS

CROSS-REFERENCE TO RELATED APPLICATIONS

This application is the National Stage of International Application No. PCT/EP2014/075058, filed Nov. 19, 2014, which claims the benefit of Great Britain application number 1321717.9, filed Dec. 9, 2013, the disclosures of which are incorporated herein by reference in their entireties.

The present invention relates to inhalable medicaments, and particularly to inhalable $\beta_2$-agonists, like formoterol.

Inhalable $\beta_2$adrenoceptor agonists (often abbreviated to "$\beta_2$-agonists") are widely used to treat respiratory diseases and particularly asthma and COPD. They are typically divided into short-acting $\beta_2$-agonists (SABAs) and long-acting $\beta_2$-agonists (LABAs). Examples of SABAs include salbutamol, levosalbutamol, terbutaline, pirbuterol, procaterol, clenbuterol, metaproterenol, fenoterol, bitolterol, ritodrine and isoprenaline. Examples of LABAs include formoterol, salmeterol, bambuterol, indacaterol and carmoterol. Many are used as pharmaceutically acceptable salts. An example of particular interest is formoterol fumarate.

Inhalable $\beta_2$-agonists are typically administered using a dry powder inhaler (DPI), a pressurised metered dose inhaler (pMDI) or a nebuliser. In these approaches, the active ingredient must be in the form of particles which are small enough to be inhaled via the mouth and into the lungs. In many instances, the active ingredients are micronised prior to formulation. This is essential where the active ingredient is not in solution. The particle size of the inhalable $\beta_2$-agonist is typically in the region of 1-5 microns (mass median aerodynamic diameter).

Inhalable $\beta_2$-agonists treat respiratory disorders by acting on $\beta_2$-adrenoceptors in the respiratory tract. However, these receptors are also located, inter alia, in the heart and blood vessels, and administration of $\beta_2$-agonists is widely documented as leading to adverse cardiac side effects. It is believed that these adverse events occur when the $\beta_2$-agonists enter the bloodstream. A common mechanism for entry of $\beta_2$-agonists into the bloodstream is that some of the particles which are too large to be inhaled deposit in the throat and are swallowed by the patient. There is a need in the art for formulations of inhalable $\beta_2$-agonists which provide the required therapeutic effect whilst minimising cardiac side effects.

This requirement is magnified for combination products. Combination products are well established in the art and are known to improve patient convenience and compliance. One example is the combination of an inhalable $\beta_2$-agonist and an inhalable corticosteroid, e.g. formoterol fumarate and budesonide. A drawback of combination products are that control over the dose of the individual active ingredients is reduced. For the inhaled corticosteroid, this is not a serious concern because the therapeutic window of inhaled corticosteroids is wide. That is, it is difficult for a patient to exceed the recommended daily intake of inhaled corticosteroid. However, the $\beta_2$-agonist is more of a concern since the therapeutic window is narrower and $\beta_2$-agonists, as previously mentioned, are associated with serious adverse effects, including cardiac side-effects.

Accordingly, the present invention provides a dry powder inhaler comprising:
a reservoir containing a dry powder formulation and an arrangement for delivering a metered dose of the medicament from the reservoir;
a cyclone deagglomerator for breaking up agglomerates of the dry powder medicament; and
a delivery passageway for directing an inhalation-induced air flow through a mouthpiece, the delivery passageway extending to the metered dose of medicament,
wherein the formulation comprises an inhalable $\beta_2$-agonist having a particle size distribution of d10<1 μm, d50=1-3 μm, d90=3.5-6 μm and NLT 99%<10 μm and a lactose carrier.

The combination of this DPI and formulation surprisingly shows a reduced systemic exposure leading to reduced side effects.

The present invention will now be described with reference to the drawings, in which.

The present invention is based on a DPI providing active metering and a cyclone deagglomerator combined with a $\beta_2$-agonist formulation which has a narrowly defined particle size distribution. The d90 value in particular is closely controlled to provide a coarser than usual powder and it has been surprisingly found that such a powder reduces systemic exposure to the $\beta_2$-agonist and hence minimises cardiac side effects.

The inhalable $\beta_2$-agonist is preferably selected form salbutamol, levosalbutamol, terbutaline, pirbuterol, procaterol, clenbuterol, metaproterenol, fenoterol, bitolterol, ritodrine, isoprenaline, formoterol, salmeterol, bambuterol, indacaterol, carmoterol or pharmaceutically acceptable salts thereof. This list includes SABAs and LABAs (defined hereinabove). An example of particular interest is formoterol fumarate, e.g. formoterol fumarate dihydrate.

The inhalable $\beta_2$-agonist may be prepared by jet milling. The process comprises the steps of providing the $\beta_2$-agonist in particulate form, jet milling the $\beta_2$-agonist and collecting the resultant micronised powder.

First, the $\beta_2$-agonist is provided in particulate form. Particulate forms of $\beta_2$-agonists are widely used in the milling process. The particles of the $\beta_2$-agonist are hard enough to be fractured during the milling process. The inhalable $\beta_2$-agonist in particulate form preferably has a Young's modulus of >0.5 GPa, more preferably >1 GPa, more preferably >5 GPa and most preferably >10 GPa. Young's modulus may be determined by nanoindentation, e.g. using an atomic force microscope (AFM).

Figure 1:
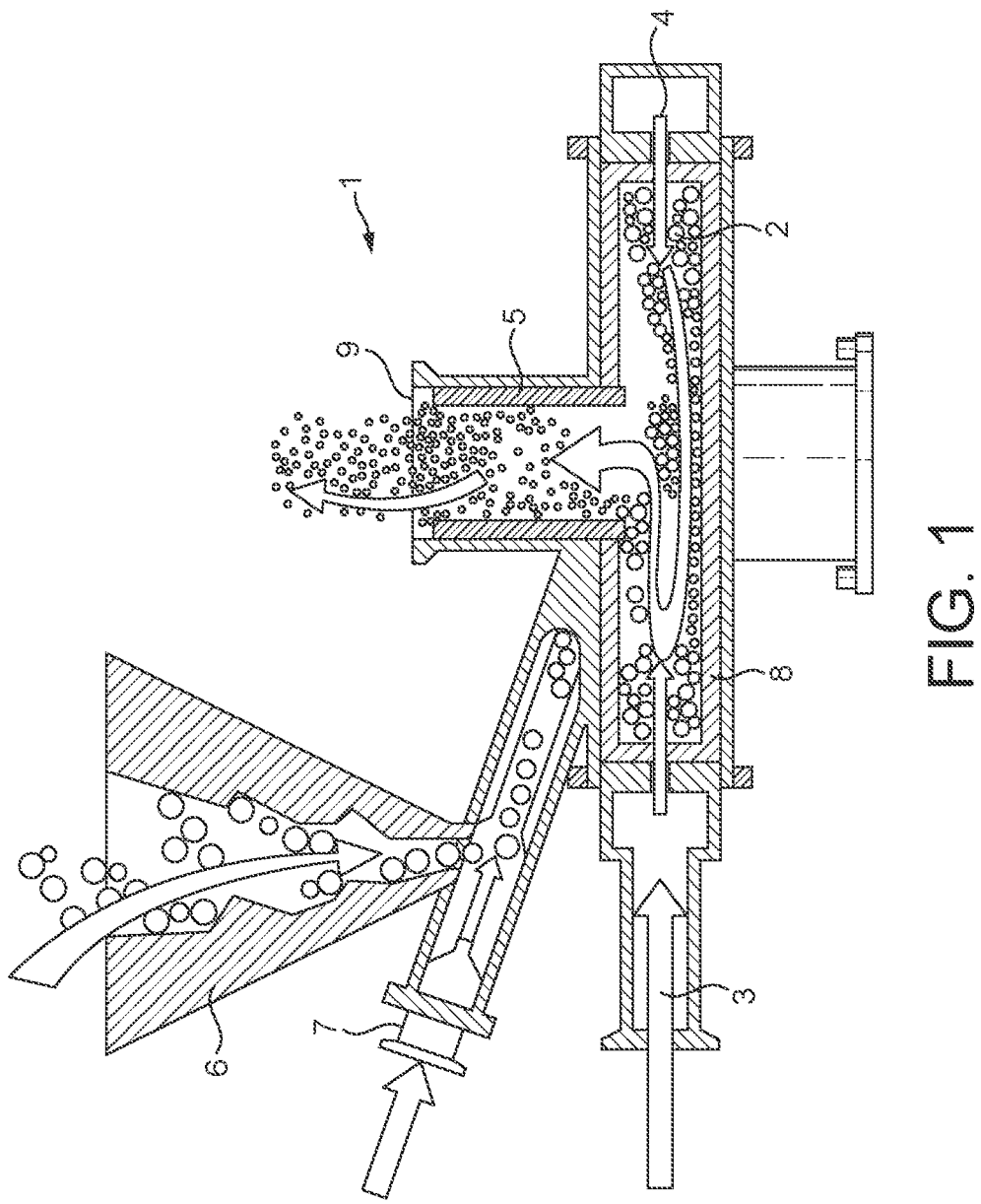
FIG. 1 shows a jet mill suitable for use with the present invention.
Figure 2:
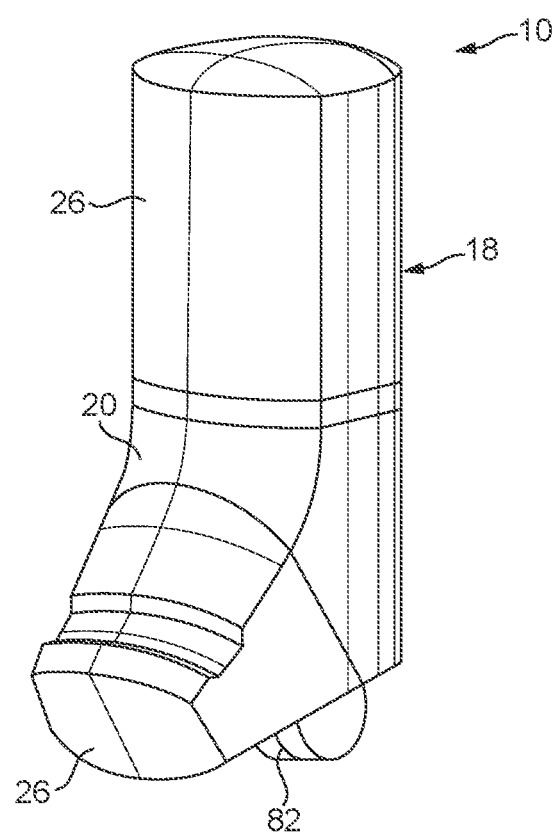
FIG. 2 is a first side isometric view of a dry powder inhaler according to a preferred embodiment.

The powder is preferably prepared by jet milling. As shown in FIG. 1, a jet mill 1 utilises a shallow cylindrical grinding chamber 2 into which a high-pressure gas is charged from interchangeable nozzles 3 spaced at regular intervals around the perimeter of the chamber 2 via a manifold 4. Gas enters the grinding chamber in the form of high-energy jets at a fixed pressure. The axes of the jets are tangential to an imaginary circle, having a radius between the outer walls of the chamber and the gas outlet port, such radius being a function of the product to be milled and of the particle size to be targeted. The fluid jets thus generate a high-speed vortex 5 into which is introduced from a feed funnel 6 the material to be micronised using a feed gas 7. The chamber 2 may be lined with a liner 8. The jet milling is typically performed under the following conditions: a feed pressure of 8.0-10 bar; a grinding pressure of 4.0-6.0 bar; and a feed rate of 1.8-2.2 Kg/h. The milled powder is discharged via an outlet 9. These conditions are particularly tailored to providing $\beta_2$-agonists suitable for the present invention. The higher feed rate distributes the energy from the grinding over a greater number of particles thereby limiting the size reduction effect.

The resulting powder is collected and is in a form suitable for inhalation.

The resulting $\beta_2$-agonist powder has the following particle size distribution d10<1 µm, d50=1-3 µm, d90=3.5-6 µm and NLT 99%<10 µm. Preferably, the $\beta_2$-agonist powder has the following particle size distribution d10=0.4-0.6, d50=1.5-2.5 and d90=3.6-5.1. Most preferably, it has the following particle size distribution d10=0.46-0.53, d50=1.68-1.92 and d90=3.68-5.07. These particle size distributions most preferably apply to the $\beta_2$-agonist, formoterol fumarate.

The particle size of the $\beta_2$-agonist powder may be measured by laser diffraction as a dry dispersion, e.g. in air, such as with a Sympatec HELOS/BF equipped with a RODOS disperser.

The formulation of the present invention is administered using a DPI. The carrier is lactose. The lactose carrier preferably has a particle size distribution of d10=20-65 µm, d50=80-120 µm, d90=130-180 µm and <10 µm=<10%. Preferably, the particle size distribution of the lactose is d10=20-65 µm, d50=80-120 µm, d90=130-180 µm and <10 µm=<6%. The lactose is preferably lactose monohydrate (α-lactose monohydrate) and may be prepared by standard techniques, e.g. sieving. The particle size distribution of the lactose may be measured by laser diffraction as a dry dispersion, using the technique described hereinabove.

The formulation may further comprise one or more additional inhalable active ingredients, preferably a corticosteroid, e.g. budesonide, beclomethasone dipropionate or fluticasone. A particularly preferred combination is formoterol fumarate and budesonide.

It is preferable that substantially all of the particles of the corticosteroid are less than 10 µm in size. This is to ensure that the particles are effectively entrained in the air stream and deposited in the lower lung, which is the site of action. Preferably, the particle size distribution of the corticosteroid is d10<1 µm, d50=<5 µm, d90=<10 µm and NLT 99%<10 µm.

The delivered dose of the $\beta_2$-agonist (the "labelled" quantity, i.e. the amount actually delivered to the patient) will depend on the nature of the $\beta_2$-agonist. By way of example, the delivered dose of formoterol fumarate, as base, is preferably 1-20 µg per actuation, with specific examples being 4.5 and 9 µg per actuation. The doses are based on the amount formoterol present (i.e. the amount is calculated without including contribution to the mass of the counterion). The delivered dose of budesonide is preferably 50-500 µg per actuation, with specific examples being 80, 160 and 320 µg per actuation. Particularly preferred delivered doses of budesonide/formoterol in µg are 80/4.5, 160/4.5 and 320/9.

The delivered dose of the active agent is measured as per the USP <601>, using the following method. A vacuum pump (MSP HCP-5) is connected to a regulator (Copley TPK 2000), which is used for adjusting the required drop pressure $P_1$ in a DUSA sampling tube (Dosage Unit Sampling Apparatus, Copley). The inhaler is inserted into a mouthpiece adaptor, ensuring an airtight seal. $P_1$ is adjusted to a pressure drop of 4.0 KPa (3.95-4.04 KPa) for the purposes of sample testing. After actuation of the inhaler, the DUSA is removed and the filter paper pushed inside with the help of a transfer pipette. Using a known amount of solvent (acetonitrile:methanol:water (40:40:20)), the mouthpiece adaptor is rinsed into the DUSA. The DUSA is shaken to dissolve fully the sample. A portion of the sample solution is transferred into a 5 mL syringe fitted with Acrodisc PSF 0.45 µm filter. The first few drops from the filter are discarded and the filtered solution is transferred into a UPLC vial. A standard UPLC technique is then used to determine the amount of active agent delivered into the DUSA. The delivered doses of the inhaler are collected at the beginning, middle and end of inhaler life, typically on three different days.

The present invention also provides a dry powder inhaler comprising the formulation as defined herein. Several types of DPI are known in the art. In a preferred embodiment of the present invention, the dry powder inhaler comprises the following features.

The preferred inhaler comprises a reservoir containing a dry powder medicament and an arrangement for delivering a metered dose of the medicament from the reservoir; a cyclone deagglomerator for breaking up agglomerates of the dry powder medicament; and a delivery passageway for directing an inhalation-induced air flow through a mouthpiece, the delivery passageway extending to the metered dose of medicament.

In a preferred form, the deagglomerator comprises:

an inner wall defining a swirl chamber extending along an axis from a first end to a second end;

a dry powder supply port in the first end of the swirl chamber for providing fluid communication between the delivery passageway of the inhaler and the first end of the swirl chamber;

at least one inlet port in the inner wall of the swirl chamber adjacent to the first end of the swirl chamber providing fluid communication between a region exterior to the deagglomerator and the first end of the swirl chamber;

an outlet port providing fluid communication between the second and of the swirl chamber and a region exterior to the deagglomerator; and vanes at the first end of the swirl chamber extending at least in part radially outwardly from the axis of the chamber, each of the vanes having an oblique surface facing at least in part in a direction transverse to the axis; whereby a breath-induced low pressure at the outlet port causes air flows into the swirl chamber through the dry powder supply port and the inlet port.

In a further preferred embodiment, the reservoir is a sealed reservoir including a dispensing port, and the inhaler further comprises a channel communicating with the dispensing port and including a pressure relief port;

a conduit providing fluid communication between an interior of the sealed reservoir and the pressure relief port of the channel; and a cup assembly movably received in the channel and including, a recess adapted to receive medicament when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

The dose metering system includes a cup received in the channel, which is movable between the dispenser port and the delivery passageway, a cup spring biasing the cup towards one of the dispenser port and the passageway, and a yoke movable between at least two positions. The yoke includes a ratchet engaging the cup and preventing movement of the cup when the yoke is in one of the positions, and allowing movement of the cup when the yoke is in another of the positions.

The inhaler includes a cyclone deagglomerator for breaking up agglomerates of the active ingredients and carrier. This occurs prior to inhalation of the powder by a patient. The deagglomerator includes an inner wall defining a swirl chamber extending along an axis from a first end to a second end, a dry powder supply port, an inlet port, and an outlet port.

The supply port is in the first and of the swirl chamber for providing fluid communication between a dry powder delivery passageway of the inhaler and the first end of the swirl chamber. The inlet port is in the inner wall of the swirl chamber adjacent to the first end of the swirl chamber and provides fluid communication between a region exterior to the deagglomerator and the swirl chamber. The outlet port provides fluid communication between the second end of the swirl chamber and a region exterior to the deagglomerator.

A breath induced low pressure at the outlet port causes air flows into the swirl chamber through the dry powder supply port and the inlet port. The air flows collide with each other and with the wall of the swirl chamber prior to exiting through the outlet port, such that the active is detached from the carrier (lactose). The deagglomerator further includes vanes at the first end of the swirl chamber for creating additional collisions and impacts of entrained powder.

A first breath-actuated air flow is directed for entraining a dry powder from an inhaler into a first end of a chamber extending longitudinally between the first end and a second end, the first air flow directed in a longitudinal direction.

A second breath-actuated airflow is directed in a substantially transverse direction into the first end of the chamber such that the air flows collide and substantially combine.

Then, a portion of the combined air flows is deflected in a substantially longitudinal direction towards a second end of the chamber, and a remaining portion of the combined air flows is directed in a spiral path towards the second end of the chamber. All the combined air flows and any dry powder entrained therein are then delivered from the second end of the chamber to a patient's mouth.

The deagglomerator ensures that particles of the actives are small enough for adequate penetration of the powder into a bronchial region of a patient's lungs during inhalation by the patient.

The inhaler preferably has a dose counter. The inhaler includes a mouthpiece for patient inhalation, a dose-metering arrangement including a pawl movable along a predetermined path during the metering of a dose of medicament to the mouthpiece by the dose-metering arrangement, and a dose counter.

In a preferred form, the dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advanced onto the spool during the metering of a dose to the mouthpiece.

The preferred inhaler includes a simple, accurate and consistent mechanical dose metering system that dispenses dry powdered medicament in discrete amounts or doses for patient inhalation, a reservoir pressure system that ensures consistently dispensed doses, and a dose counter indicating the number of doses remaining in the inhaler.

With reference to the drawings, the inhaler 10 generally includes a housing 18, and an assembly 12 received in the housing (see FIG. 3). The housing 18 includes a case 20 having an open end 22 and a mouthpiece 24 for patient inhalation, a cap 26 secured to and closing the open end 22 of the case 20, and a cover 28 pivotally mounted to the case 20 for covering the mouthpiece 24 (see FIGS. 2, 3 and 10). The housing 18 is preferably manufactured from a plastic such as polypropylene, acetal or moulded polystyrene, but may be manufactured from metal or another suitable material.

The internal assembly 12 includes a reservoir 14 for containing dry powered medicament in bulk form, a deagglomerator 10' that breaks down the medicament between a delivery passageway 34 and the mouthpiece 24, and a spacer 38 connecting the reservoir to the deagglomerator.

The reservoir 14 is generally made up of a collapsible bellows 40 and a hopper 42 having an dispenser port 44 (see FIGS. 3-6, 8 and 9) for dispensing medicament upon the bellows 40 being at least partially collapsed to reduce the internal volume of the reservoir.

The hopper 42 is for holding the dry powder medicament in bulk form and has an open end 46 closed by the flexible accordion-like bellows 40 in a substantially air-tight manner.

Figures 8, 9:
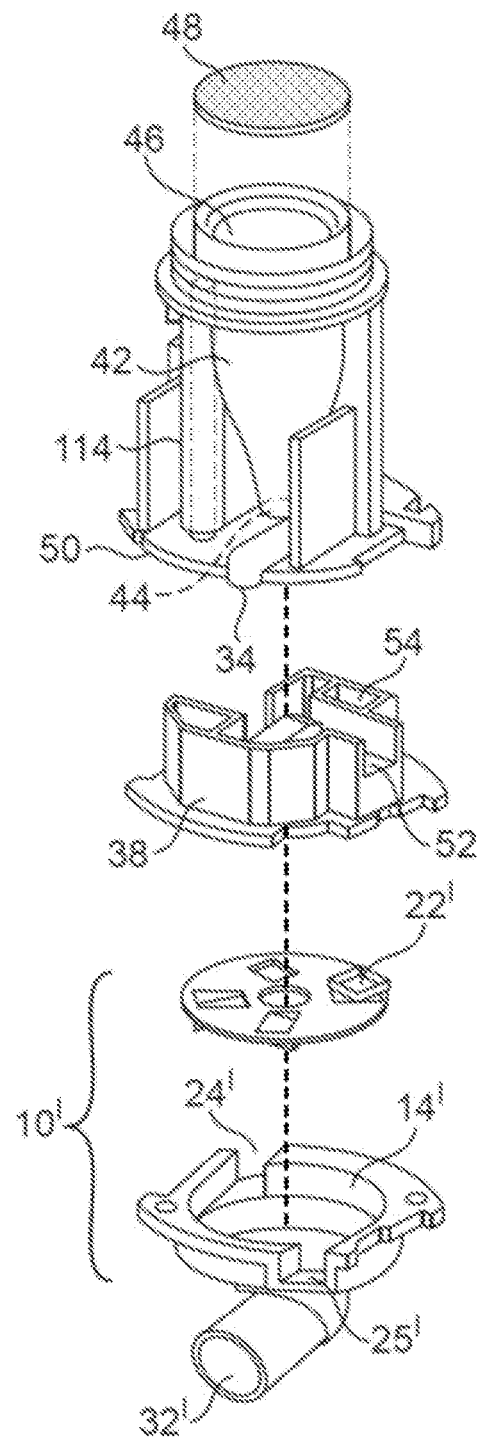
FIG. 8 is an exploded first side isometric view of a hopper and a deagglomerator of the inhaler of FIG. 2.
FIG. 9 is an exploded second side isometric view of the hopper and a swirl chamber roof of the deagglomerator of the inhaler of FIG. 2.

An air filter 48 covers the open end 46 of the hopper 42 and prevents dry powder medicament from leaking from the hopper 42 (see FIG. 8).

A base 50 of the hopper 42 is secured to a spacer 38, which is in turn secured to the deagglomerator 10' (see FIGS. 4-6, 8 and 9). The hopper 42, the spacer 38, and the deagglomerator 10' are preferably manufactured from a plastic such as polypropylene, acetal or moulded polystyrene, but may be manufactured from metal or another suitable material.

The hopper 42, the spacer 38 and the deagglomerator 10' are connected in a manner that provides an air tight seal between the parts. For this purpose heat or cold sealing, laser welding or ultrasonic welding could be used, for example.

The spacer 38 and the hopper 42 together define the medicament delivery passageway 34, which preferably includes a venturi 36 (see FIG. 17) for creating an entraining air flow. The spacer 38 defines a slide channel 52 communicating with the dispenser port 44 of the hopper 42, and a chimney 54 providing fluid communication between the medicament delivery passageway 34 and a supply port 22' of the deagglomerator 10' (see FIGS. 8 and 9). The slide channel 52 extends generally normal with respect to the axis "A" of the inhaler 10.

The deagglomerator 10' breaks down agglomerates of dry powder medicament before the dry powder leaves the inhaler 10 through the mouthpiece 24.

Referring to FIGS. 18-23, the deagglomerator 10' breaks down agglomerates of medicament, or medicament and carrier, before inhalation of the medicament by a patient.

In general, the deagglomerator 10' includes an inner wall 12' defining a swirl chamber 14' extending along an axis A' from a first end 18' to a second end 20'. The swirl chamber 14' includes circular cross-sectional areas arranged transverse to the axis A', that decrease from the first and 18' to the second end 20' of the swirl chamber 14', such that any air flow traveling from the first end of the swirl chamber to the second end will be constricted and at least in part collide with the inner wall 12' of the chamber.

Preferably, the cross-sectional areas of the swirl chamber 14' decrease monotonically. In addition, the inner wall 12' is preferably convex, i.e., arches inwardly towards the axis A', as shown best in FIG. 23.

Figure 18:
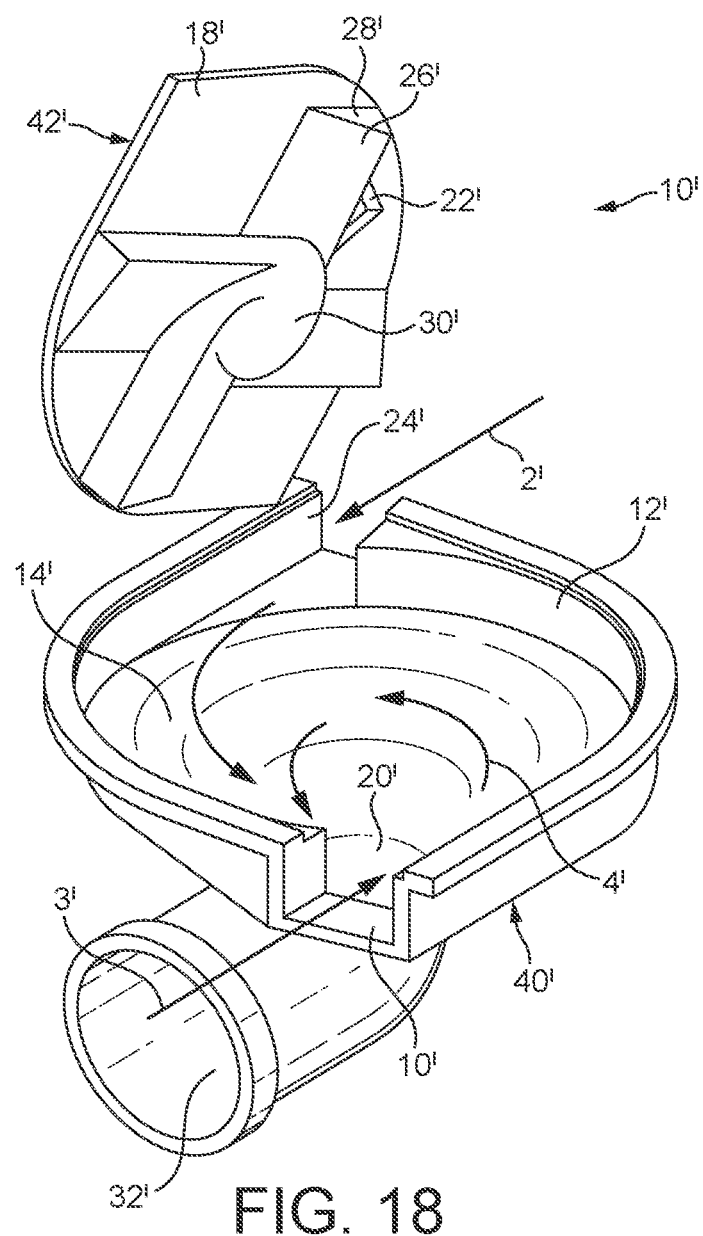
FIG. 18 is an exploded isometric view of a deagglomerator according to the present disclosure.
Figure 19:
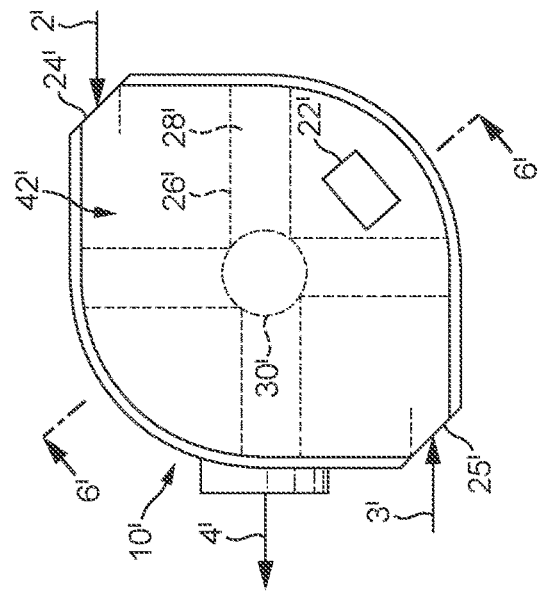
FIG. 19 is a side elevation view of the deagglomerator of FIG. 18.
Figure 20:
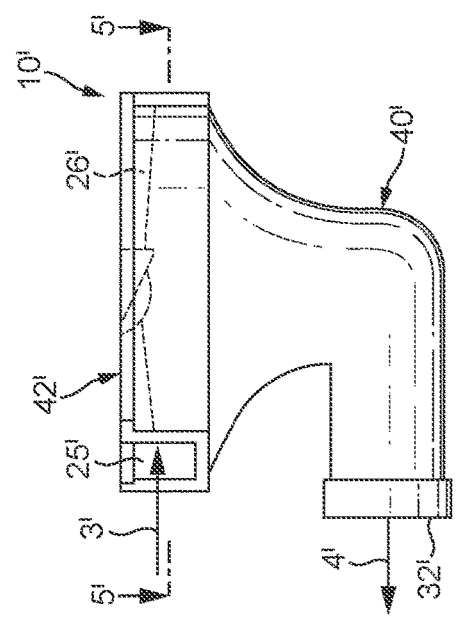
FIG. 20 is a top plan view of the deagglomerator of FIG. 18.
Figure 21:
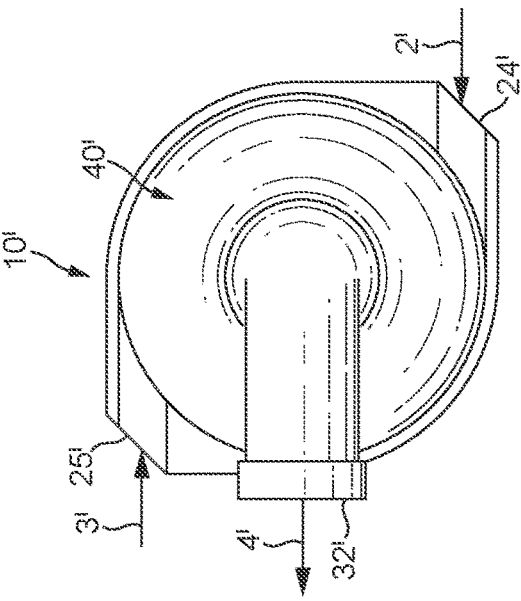
FIG. 21 is a bottom plan view of the deagglomerator of FIG. 18.
Figure 22:
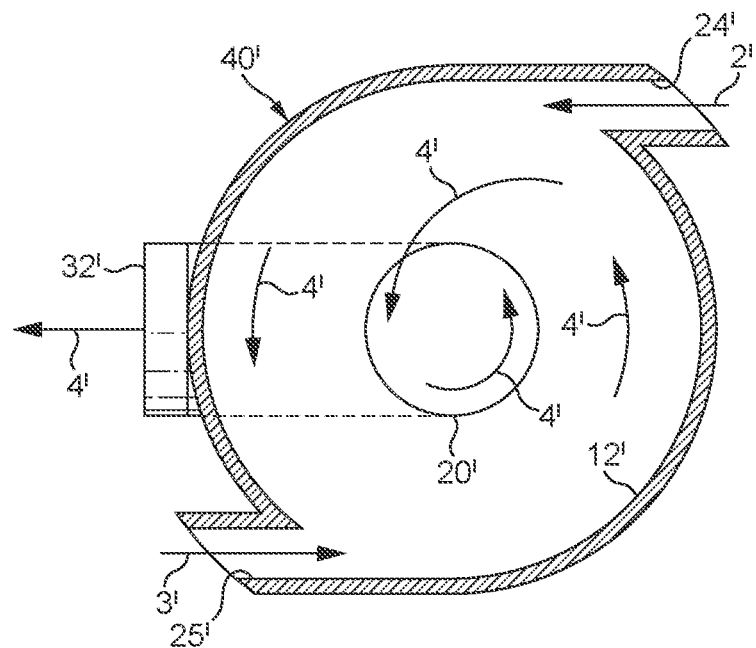
FIG. 22 is a sectional view of the deagglomerator of FIG. 18 taken along line 5'-5' of FIG. 19.
Figure 23:
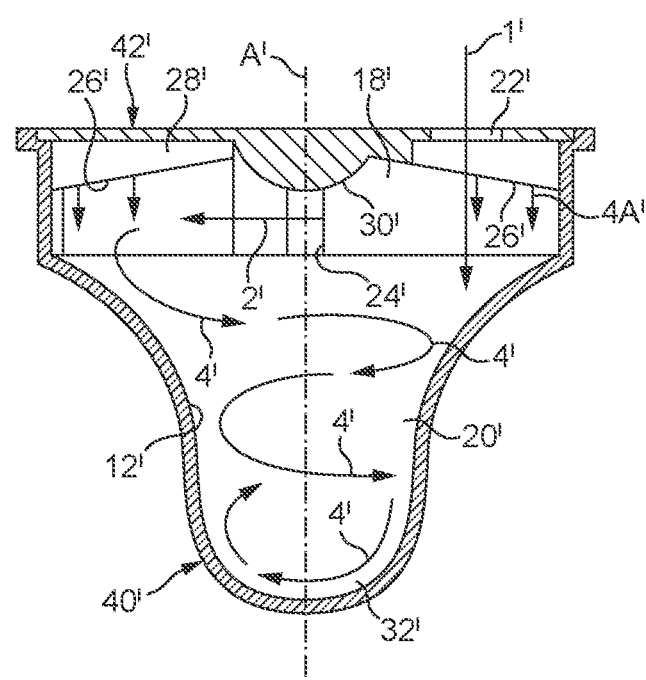
FIG. 23 is a sectional view of the deagglomerator of FIG. 18 taken along line 6'-6' of FIG. 20.

As shown in FIGS. 18, 20 and 23, the deagglomerator 10' also includes a dry powder supply port 22' in the first end 18' of the swirl chamber 14' for providing fluid communication between a dry powder delivery passageway of an inhaler and the first end 16' of the swirl chamber 14'. Preferably, the dry powder supply port 22' faces in a direction substantially parallel with the axis A' such that an air flow, illustrated by arrow 1' in FIG. 23, entering the chamber 14' through the supply port 22' is at least initially directed parallel with respect to the axis A' of the chamber.

Referring to FIGS. 18-23, the deagglomerator 10' additionally includes at least one inlet port 24' in the inner wall 12' of the swirl chamber 14' adjacent to or near the first end 18' of the chamber providing fluid communication between a region exterior to the deagglomerator and the first end 18' of the swirl chamber 14'. Preferably, the at least one inlet port comprises two diametrically opposed inlet ports 24', 25' that extend in a direction substantially transverse to the axis A' and substantially tangential to the circular cross-section of the swirl chamber 14'. As a result, air flows, illustrated by arrows 2' and 3' in FIGS. 18 and 22, entering the chamber 14' through the inlet ports are at least initially directed transverse with respect to the axis A' of the chamber and collide with the air flow 1' entering through the supply port 22' to create turbulence. The combined air flows, illustrated by arrow 4' in FIGS. 22 and 23, than collide with the inner wall 12' of the chamber 14', form a vortex, and create additional turbulence as they move towards the second end 20' of the chamber.

Referring to FIGS. 18-20 and 23, the deagglomerator 10' includes vanes 26' at the first end 18' of the swirl chamber 14' extending at least in part radially outwardly from the axis A' of the chamber. Each of the vanes 26' has an oblique surface 28' facing at least in part in a direction transverse to the axis A' of the chamber. The vanes 26' are sized such that at least a portion 4A' of the combined air flows 4' collide with the oblique surfaces 28', as shown in FIG. 23. Preferably, the vanes comprise four vanes 26', each extending between a hub 30' aligned with the axis A' and the wall 12' of the swirl chamber 14'.

As shown in FIGS. 18-23, the deagglomerator 10' further includes an outlet port 32' providing fluid communication between the second end 20' of the swirl chamber 14' and a region exterior to the deagglomerator. A breath induced low pressure at the outlet port 32' causes the air flow 1' through the supply port 22' and the air flows 2',3' through the inlet ports and draws the combined air flow 4' through the swirl chamber 14'. The combined air flow 4' then exits the deagglomerator through the outlet port 32'. Preferably the outlet port 32' extends substantially transverse to the axis A', such that the air flow 4' will collide with an inner wall of the outlet port 32' and create further turbulence.

During use of the deagglomerator 10' in combination with the inhaler, patient inhalation at the outlet port 32' causes air flows 1',2',3' to enter through, respectively, the dry powder supply port 22' and the inlet ports. Although not shown, the air flow 1' through the supply port 22' entrains the dry powder into the swirl chamber 14'. The air flow 1' and entrained dry powder are directed by the supply port 22' into the chamber in a longitudinal direction, while the air flows 2',3' from the inlet ports are directed in a transverse direction, such that the air flows collide and substantial combine.

A portion of the combined air flow 4' and the entrained dry powder then collide with the oblique surfaces 28' of the vanes 26' causing particles and any agglomerates of the dry powder to impact against the oblique surfaces and collide with each other. The geometry of the swirl chamber 14' causes the combined air flow 4' and the entrained dry powder to follow a turbulent, spiral path, or vortex, through the chamber. As will be appreciated, the decreasing cross-sections of the swirl chamber 14' continuously changes the direction and increases the velocity of the spiralling combined air flow 4' and entrained dry powder. Thus, particles and any agglomerates of the dry powder constantly impact against the wall 12' of the swirl chamber 14' and collide with each other, resulting in a mutual grinding or shattering action between the particles and agglomerates. In addition, particles and agglomerates deflected off the oblique surfaces 28' of the vanes 26' cause further impacts and collisions.

Upon exiting the swirl chamber 14', the direction of the combined air flow 4 and the entrained dry powder is again changed to a transverse direction with respect to the axis A', through the outlet port 32'. The combined air flow 4' and the entrained dry powder retain a swirl component of the flow, such that the air flow 4' and the entrained dry powder spirally swirls through the outlet port 32'. The swirling flow causes additional impacts in the outlet port 32' so as to result in further breaking up of any remaining agglomerates prior to being inhaled by a patient.

As shown in FIGS. 18-23, the deagglomerator is preferably assembly from two pieces: a cup-like base 40' and a cover 42'. The base 40' and the cover 42' are connected to form the swirl chamber 14'. The cup-like base 40' includes the wall 12' and the second and 20' of the chamber and defines the outlet port 32'. The base 40' also includes the inlet ports of the swirl chamber 14'. The cover 42' forms the vanes 26' and defines the supply port 22'.

The base 40' and the cover 42' of the deagglomerator are preferably manufactured from a plastic such as polypropylene, acetal or moulded polystyrene, but may be manufactured from metal or another suitable material. Preferably, the cover 42' includes an anti-static additive, so that dry powder will not cling to the vanes 26'. The base 40' and the cover 42' are then connected in a manner that provides an air tight seal between the parts. For this purpose heat or cold sealing, laser welding or ultra-sonic welding could be used, for example.

Although the inhaler 10 is shown with a particular deagglomerator 10', the inhaler 10 is not limited to use with the deagglomerator shown and can be used with other types of deagglomerators or a simple swirl chamber.

Figure 3:
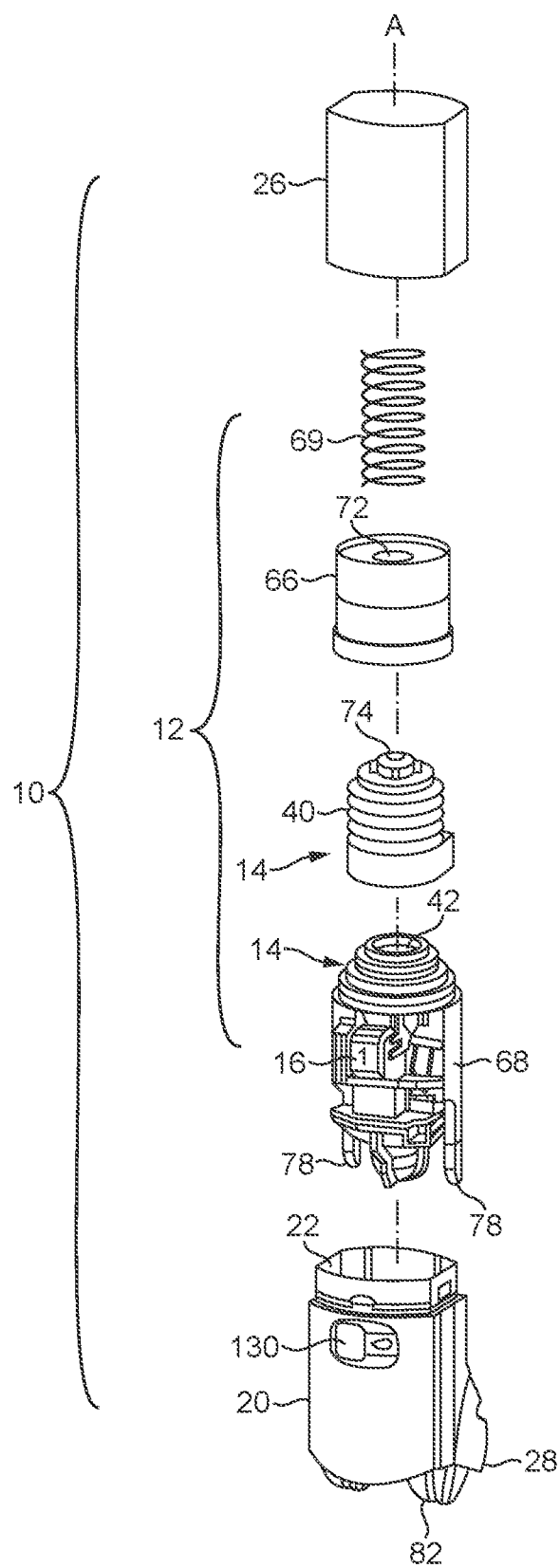
FIG. 3 is an exploded, second side isometric view of the inhaler of FIG. 2.
Figure 4:
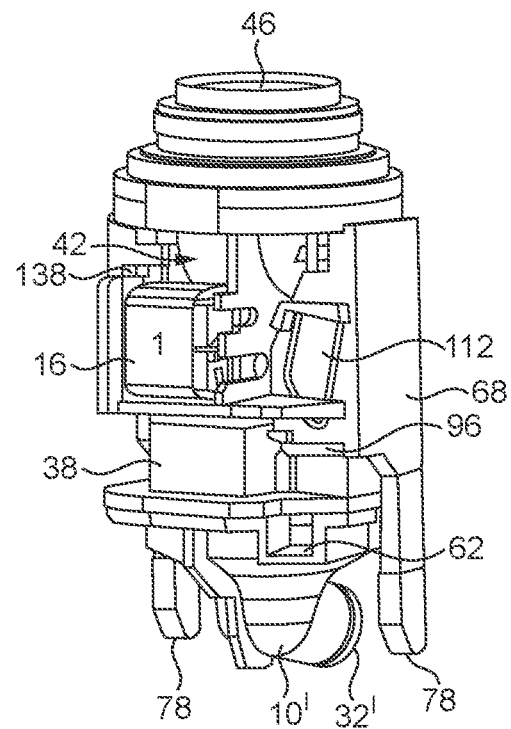
FIG. 4 is a second side isometric view of a main assembly of the inhaler of FIG. 2.
Figure 5:
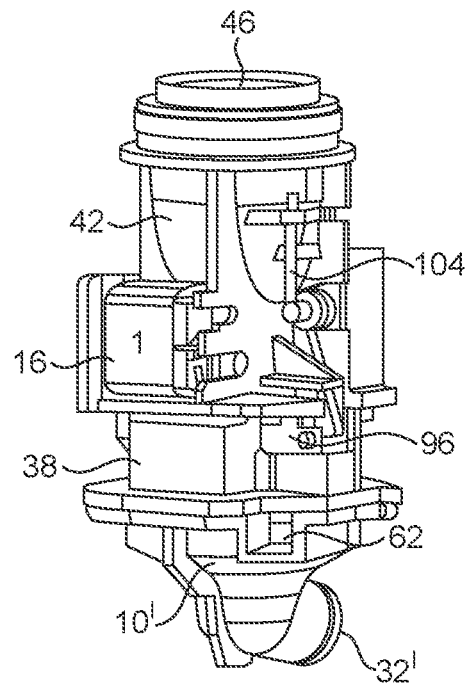
FIG. 5 is a second side isometric view of the main assembly of the inhaler of FIG. 2, shown with a yoke removed.

The dose metering system includes a first yoke 66 and a second yoke 68 mounted on the internal assembly 12 within the housing 18, and movable in a linear direction parallel with an axis "A" of the inhaler 10 (see FIG. 3). An actuation spring 69 is positioned between the cap 26 of the housing 18 and the first yoke 66 for biasing the yokes in a first direction towards the mouthpiece 24. In particular, the actuation spring 69 biases the first yoke 66 against the bellows 40 and the second yoke 68 against cams 70 mounted on the mouthpiece cover 28 (see FIG. 10).

Figure 10:
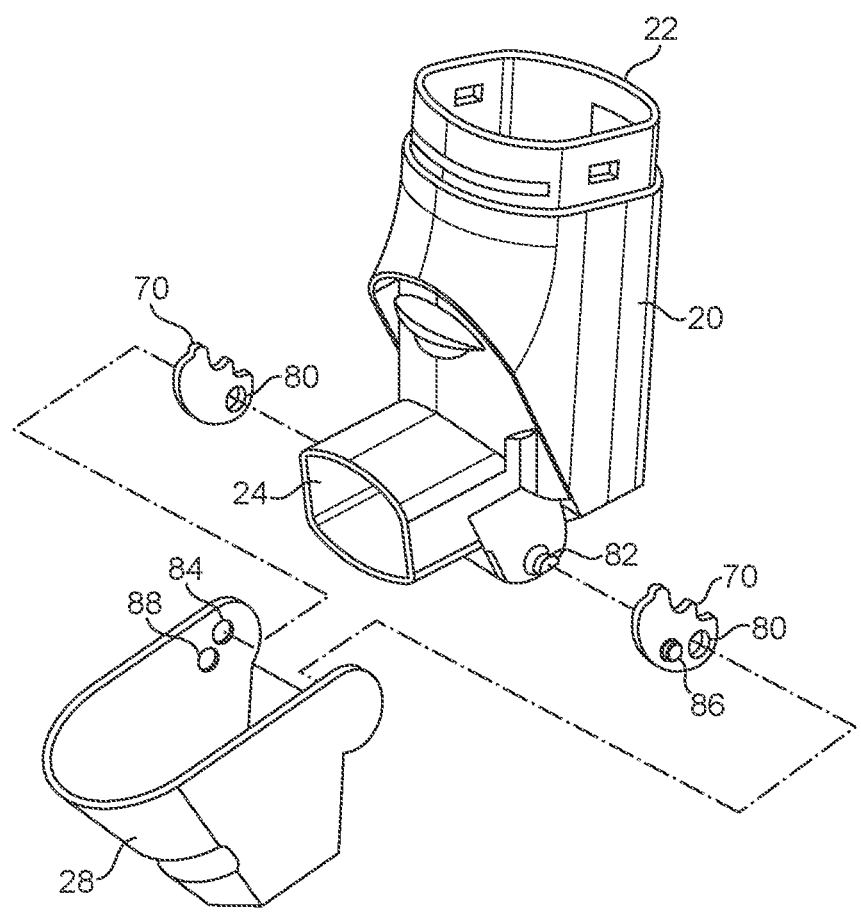
FIG. 10 is an exploded first side isometric view of a case, cams and a mouthpiece cover of the inhaler of FIG. 2.
Figure 11:
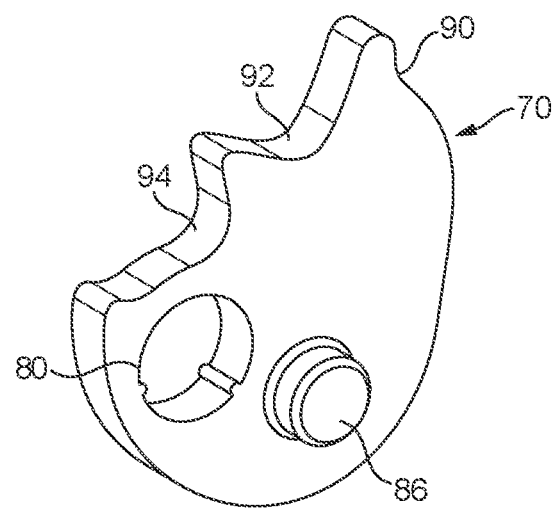
FIG. 11 is an enlarged side isometric view of one of the cams of the inhaler of FIG. 2.

The first yoke 66 includes an opening 72 that receives and retains a crown 74 of the bellows 40 such that the first yoke 66 pulls and expands the bellows 40 when moved towards the cap 26, i.e., against the actuation spring 69 (see FIG. 3). The second yoke 68 includes a belt 76, which receives the first yoke 66, and two cam followers 78 extending from the belt in a direction opposite the first yoke 66 (see FIGS. 4, 12 and 13), towards the cams 70 of the mouthpiece cover 28 (FIGS. 10 and 11).

The dose metering system also includes the two cams 70 mounted on the mouthpiece cover 28 (see FIGS. 10 and 11), and movable with the cover 28 between open and closed positions. The cams 70 each include an opening 80 for allowing outwardly extending hinges 82 of the case 20 to pass therethrough and be received in first recesses 84 of the cover 28. The cams 70 also include bosses 86 extending outwardly and received in second recesses 88 of the cover 28, such that the cover 28 pivots about the hinges 82 and the cams 70 move with the cover 28 about the hinges.

Each cam 70 also includes first, second and third cam surfaces 90,92,94, and the cam followers 78 of the second yoke 68 are biased against the cam surfaces by the actuation spring 69. The cam surfaces 90,92,94 are arranged such the cam followers 78 successively engage the first cam surfaces 90 when the cover 28 is closed, the second cam surfaces 92 when the cover 28 is partially opened, and the third cam surfaces 94 when the cover 28 is fully opened. The first cam surfaces 90 are spaced further from the hinges 82 than the second and the third cam surfaces, while the second cam surfaces 92 are spaced further from the hinges 82 than the third cam surfaces 94. The cams 70, therefore, allow the yokes 66,68 to be moved by the actuation spring 69 parallel with the axis "A" of the inhaler 10 in the first direction (towards the mouthpiece 24) through first, second and third positions as the cover 28 is opened. The cams 70 also push the yokes 66, 68 in a second direction parallel with the axis "A" (against the actuation spring 69 and towards the cap 26 of the housing 18) through the third, the second and the first positions as the cover 28 is closed.

The dose metering system further includes a cup assembly 96 movable between the dispenser port 44 of the reservoir 14 and the delivery passageway 34. The cup assembly 96 includes a medicament cup 98 mounted in a sled 100 slidably received in the slide channel 52 of the spacer 38 below the hopper 42 (see FIGS. 6 and 7). The medicament cup 98 includes a recess 102 adapted to receive medicament from the dispenser port 44 of the reservoir 14 and sized to hold a predetermined dose of dry powdered medicament when filled. The cup sled 100 is biased along the slide channel 52 from the dispenser port 44 of the hopper 42 towards the delivery passageway 34 by a cup spring 104, which is secured on the hopper 42 (see FIGS. 5 and 6).

Figure 6:
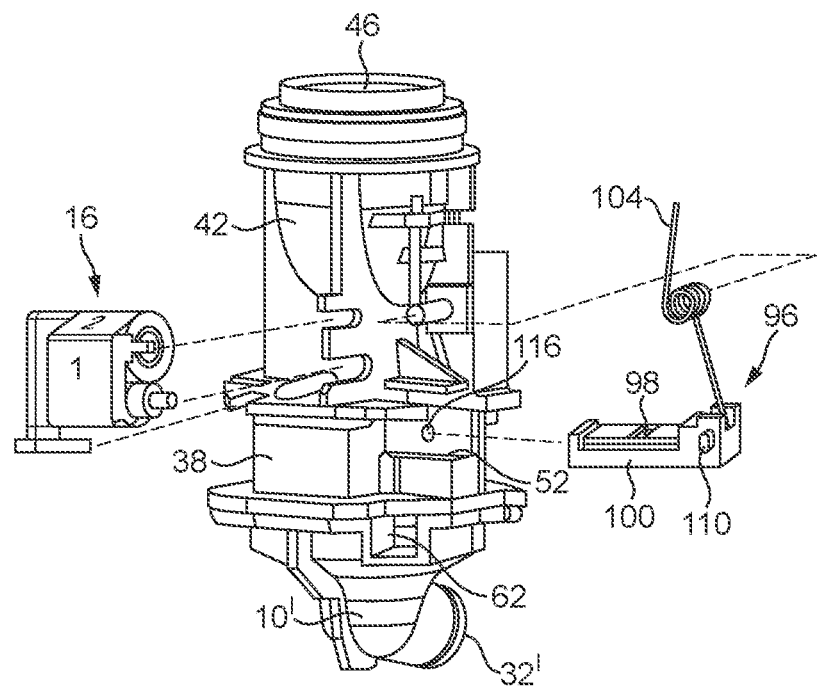
FIG. 6 is an exploded first side isometric view of the main assembly of the inhaler of FIG. 2.
Figure 12:
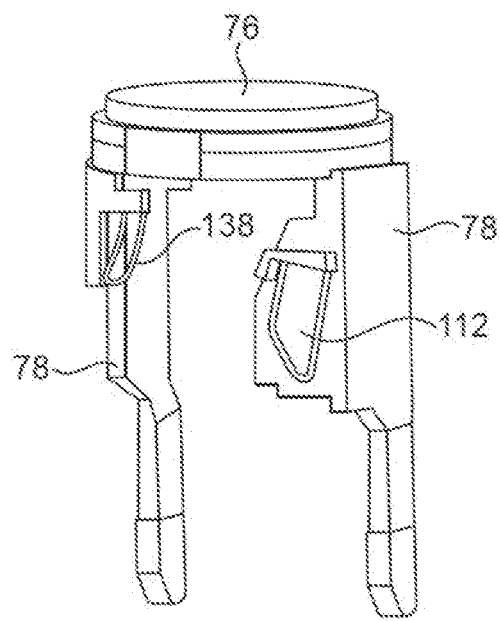
FIG. 12 is a second side isometric view of the yoke of the inhaler of FIG. 2.
Figure 13:
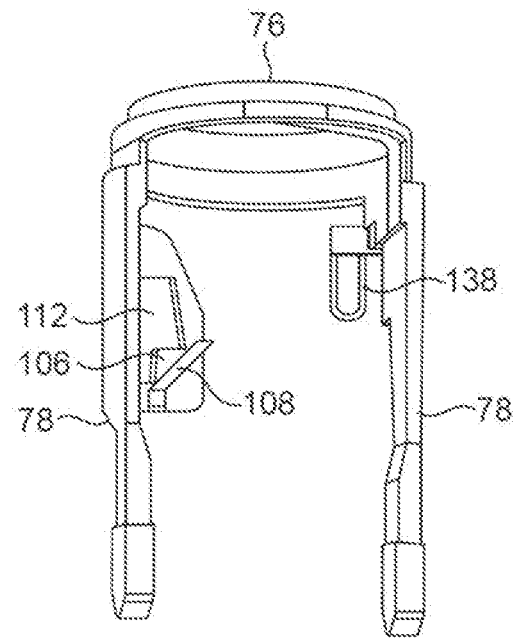
FIG. 13 is a first side isometric view of the yoke of the inhaler of FIG. 2, showing a ratchet and a push bar of the yoke.

The dose metering system also includes a ratchet 106 and a push bar 108 on one of the cam followers 78 of the second yoke 68 that engage a boss 110 of the cup sled 100 (see FIGS. 6, 12 and 13). The ratchet 106 is mounted on a flexible flap 112 and is shaped to allow the boss 110 of the sled 100 to depress and pass over the ratchet 106, when the boss 110 is engaged by the push bar 108. Operation of the dose metering system is discussed below.

The reservoir pressure system includes a pressure relief conduit 114 in fluid communication with the interior of the reservoir 14 (see FIGS. 8 and 9), and a pressure relief port 116 in a wall of the slide channel 52 (see FIGS. 6 and 9) providing fluid communication with the pressure relief conduit 114 of the hopper 42.

Figure 7:
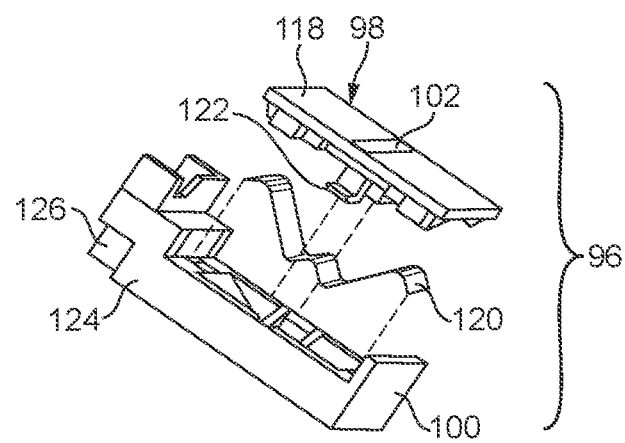
FIG. 7 is an exploded enlarged isometric view of a medicament cup of the inhaler of FIG. 2.

The medicament cup assembly 96 includes a first sealing surface 118 adapted to seal the dispenser port 44 upon the cup assembly being moved to the delivery passageway 34 (see FIGS. 6 and 7). A sealing spring 120 is provided between the sled 100 and the cup 98 for biasing the medicament cup 98 against a bottom surface of the hopper 42 to seal the dispenser port 44 of the reservoir 14. The cup 98 includes clips 122 that allow the cup to be biased against the reservoir, yet retain the cup in the sled 100.

The sled 100 includes a second sealing surface 124 adapted to seal the pressure relief port 116 when the recess 102 of the cup 98 is aligned with the dispenser port 44, and an indentation 126 (see FIG. 7) adapted to unseal the pressure relief port 116 when the first sealing surface 118 is aligned with the dispenser port 44. Operation of the pressure system is discussed below.

The dose counting system 16 is mounted to the hopper 42 and includes a ribbon 128, having successive numbers or other suitable indicia printed thereon, in alignment with a transparent window 130 provided in the housing 18 (see FIG. 3). The dose counting system 16 includes a rotatable bobbin 132, an indexing spool 134 rotatable in a single direction, and the ribbon 128 rolled and received on the bobbin 132 and having a first end 127 secured to the spool 134, wherein the ribbon 128 unrolls from the bobbin 132 so that the indicia is successively displayed as the spool 134 is rotated or advanced.

The spool 134 is arranged to rotate upon movement of the yokes 66,68 to effect delivery of a dose of medicament from the reservoir 14 into the delivery passageway 34, such that the number on the ribbon 128 is advanced to indicate that another dose has been dispensed by the inhaler 10. The ribbon 128 can be arranged such that the numbers, or other suitable indicia, increase or decrease upon rotation of the spool 134. For example, the ribbon 128 can be arranged such that the numbers, or other suitable indicia, decrease upon rotation of the spool 134 to indicate the number of doses remaining in the inhaler 10.

Alternatively, the ribbon 128 can be arranged such that the numbers, or other suitable indicia, increase upon rotation of the spool 134 to indicate the number of doses dispensed by the inhaler 10.

The indexing spool 134 preferably includes radially extending teeth 136, which are engaged by a pawl 138 extending from one of the cam followers 78 (see FIGS. 4 and 12) of the second yoke 68 upon movement of the yoke to rotate, or advance, the indexing spool 134. More particularly, the pawl 138 is shaped and arranged such that it engages the teeth 136 and advances the indexing spool 134 only upon the mouthpiece 24 cover 28 being closed and the yokes 66,68 moved back towards the cap 26 of the housing 18.

Figure 15:
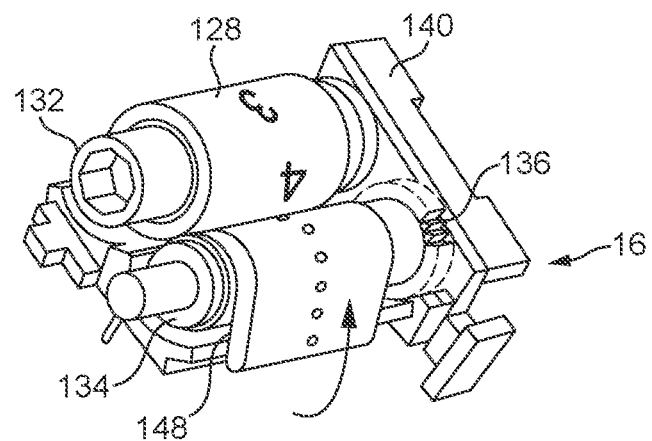
FIG. 15 is an enlarged isometric view of a dose counter of the inhaler of FIG. 2.
Figure 16:
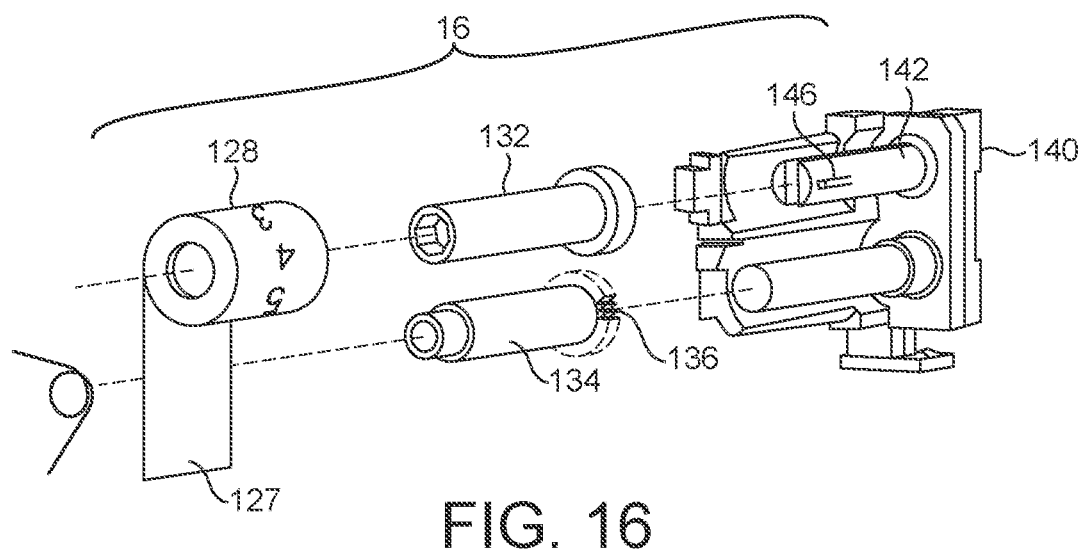
FIG. 16 is an exploded enlarged isometric view of the dose counter of the inhaler of FIG. 2.

The dose counting system 16 also includes a chassis 140 that secures the dose counting system to the hopper 42 and includes shafts 142,144 for receiving the bobbin 132 and the indexing spool 134. The bobbin shaft 142 is preferably forked and includes radially nubs 146 for creating a resilient resistance to rotation of the bobbin 132 on the shaft 142. A clutch spring 148 is received on the end of the indexing spool 134 and locked to the chassis 140 to allow rotation of the spool 134 in only a single direction (anticlockwise as shown in FIG. 15). Operation of the dose counting system 16 is discussed below.

Figure 14:
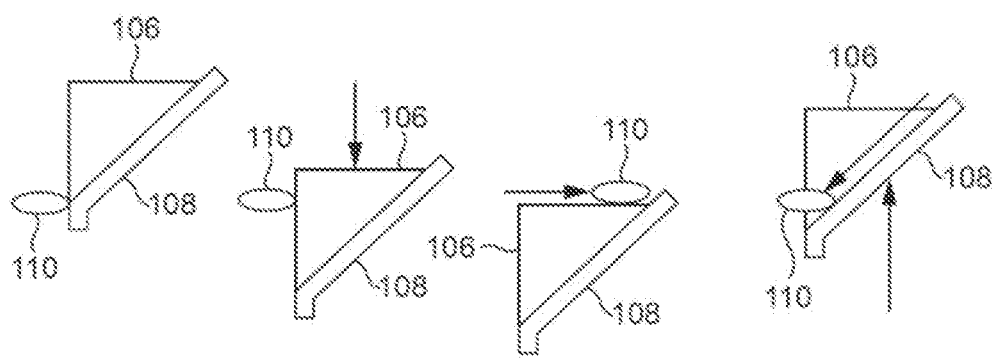
FIG. 14 is a schematic illustration of lateral movement of a boss of the medicament cup in response to longitudinal movement of the ratchet and the push bar of the yoke of the inhaler of FIG. 2.

FIG. 14 illustrates the relative movements of the boss 110 of the cup sled 100, and the ratchet 106 and the push bar 108 of the second yoke 68 as the mouthpiece cover 28 is opened and closed. In the first position of the yokes 66,68 (wherein the cover 28 is closed and the cam followers 78 are in contact with the first cam surfaces 90 of the cams 70), the ratchet 106 prevents the cup spring 104 from moving the cup sled 100 to the delivery passageway 34. The dose metering system is arranged such that when the yokes are in the first position, the recess 102 of the medicament cup 98 is directly aligned with the dispenser port 44 of the reservoir 14 and the pressure relief port 116 of the spacer 38 is sealed by the second sealing surface 124 of the cup sled 100.

Upon the cover 28 being partially opened such that the second cam surfaces 92 of the cams 70 engage the cam followers 78, the actuator spring 69 is allowed to move the yokes 66,68 linearly towards the mouthpiece 24 to the second position and partially collapse the bellows 40 of the medicament reservoir 14. The partially collapsed bellows 40 pressurizes the interior of the reservoir 14 and ensures medicament dispensed from the dispenser port 44 of the reservoir fills the recess 102 of the medicament cup 98 such that a predetermined dose is provided. In the second position, however, the ratchet 106 prevents the cup sled 100 from being moved to the delivery passageway 34, such that the recess 102 of the medicament cup 98 remains aligned with the dispenser port 44 of the reservoir 14 and the pressure relief port 116 of the spacer 38 remains sealed by the second sealing surface 124 of the cup assembly 96.

Upon the cover 28 being fully opened such that the third cam surfaces 94 engage the cam followers 78, the actuator spring 69 is allowed to move the yokes 66,68 further towards the mouthpiece 24 to the third position. When moved to the third position, the ratchet 106 disengages, or falls below the boss 110 of the cup sled 100 and allows the cup sled 100 to be moved by the cup spring 104, such that the filled recess 102 of the cup 98 is position in the venturi 36 of the delivery passageway 34 and the dispenser port 44 of the reservoir 14 is sealed by the first sealing surface 118 of the cup assembly 96. In addition, the pressure relief port 116 is uncovered by the indentation 126 in the side surface of the sled 100 to release pressure from the reservoir 14 and allow the bellows 40 to further collapse and accommodate the movement of the yokes 66,68 to the third position. The inhaler 10 is then ready for inhalation by a patient of the dose of medicament placed in the delivery passageway 34.

Figure 17:
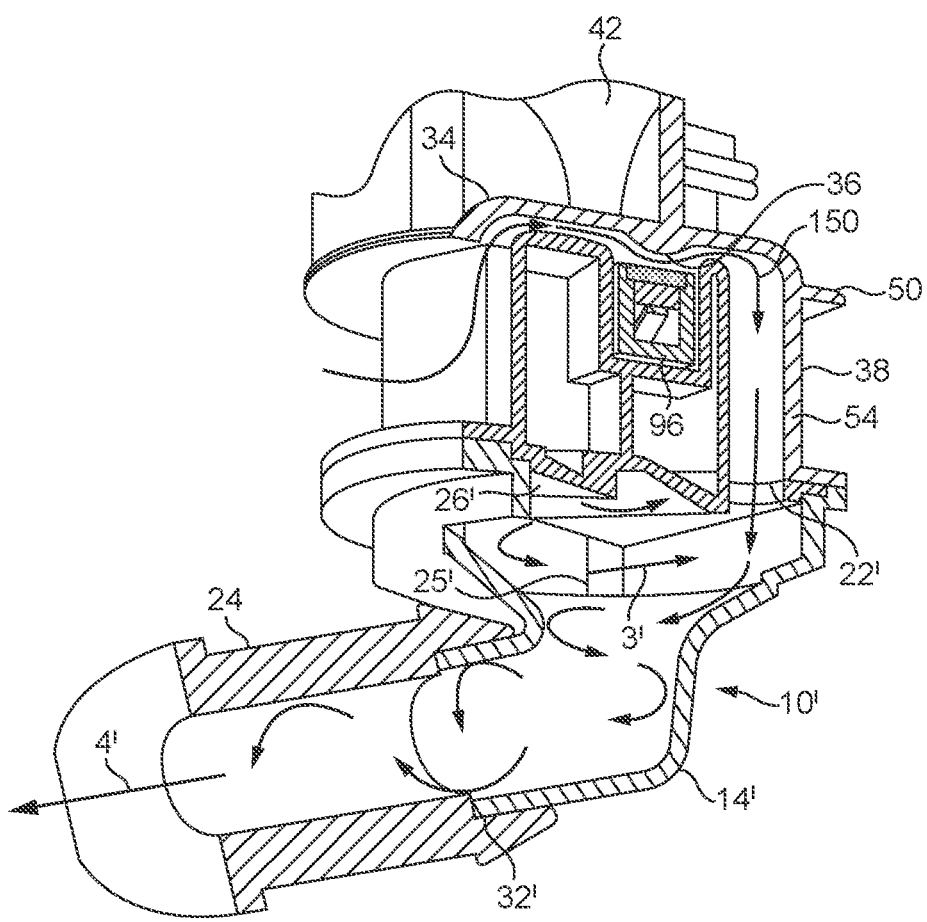
FIG. 17 is an enlarged isometric view, partially in section, of a portion of the inhaler of FIG. 2 illustrating medicament inhalation through the inhaler.

As shown in FIG. 17, a breath-induced air stream 4' diverted through the delivery passageway 34 passes through the venturi 36, entrains the medicament and carries the medicament into the deagglomerator 10' of the inhaler 10. Two other breath-induced air streams 2', 3' (only one shown) enter the deagglomerator 10' through the diametrically opposed inlet ports 24', 25' and combine with the medicament entrained air stream 150 from the delivery passageway 34. The combined flows 4' and entrained dry powder medicament then travel to the outlet port 32' of the deagglomerator and pass through the mouthpiece 24 for patient inhalation.

Once inhalation is completed, the mouthpiece cover 28 can be closed. When the cover 28 is closed, the trigger cams 70 force the yokes 66,68 upwardly such that the first yoke 66 expands the bellows 40, and the pawl 138 of the second yoke 68 advances the indexing spool 134 of the dose counting system 16 to provide a visual indication of a dose having been dispensed. In addition, the cup assembly 96 is forced back to the first position by the pusher bar 108 of the upwardly moving second yoke 68 (see FIG. 14) such that the boss 110 of the cup sled 100 is engaged and retained by the ratchet 106 of the second yoke 68.

The present invention also provides the inhaler of any aspect and embodiment of the invention for use in treating a respiratory disease. In particular, the respiratory disease may be asthma or chronic obstructive pulmonary disease (COPD).

In any aspect of the invention, it is envisaged that the asthma may be any severity of asthma, for example the asthma may be mild, mild to moderate, moderate, moderate to severe, or severe asthma. Such asthma may be classified as GINA stage 1, 2, 3 or 4 according to the Global Initiative for Asthma (GINA) guidelines, as would be understood by a person of skill in the art.

The present invention will now be described with reference to the examples, which are not intended to be limiting.

EXAMPLES

Example 1

Two samples of formoterol fumarate dihydrate were micronised by jet milling. The two batches were assigned codes 7544MA (conventional milling) and 7544MO (invention). The micronisation conditions are set out in Table 1.

TABLE 1

Micronisation conditions

| Process Parameter | Micronised code 7544MA | Micronised code 7544MO |
|---|---|---|
| Feed pressure | 9.5-10.0 bar | 8.0-10.0 bar |
| Grinding pressure | 6.0 bar | 5.0 bar |
| Feed rate | 0.5 ± 5% Kg/hour | 2.0 ± 10% Kg/hour |
| Gas | Nitrogen | Nitrogen |

The process for batch 7544MO uses a lower grinding pressure and a higher feed rate than for batch 7544MA. As such, the process for batch 7544MO utilises a lower energy to micronise formoterol than for batch 7544MA. This is the reason that the batches made by the 7544MO process have consistently higher d90 diameter than those of the batches made by the 7544MA process.

Figure 24:
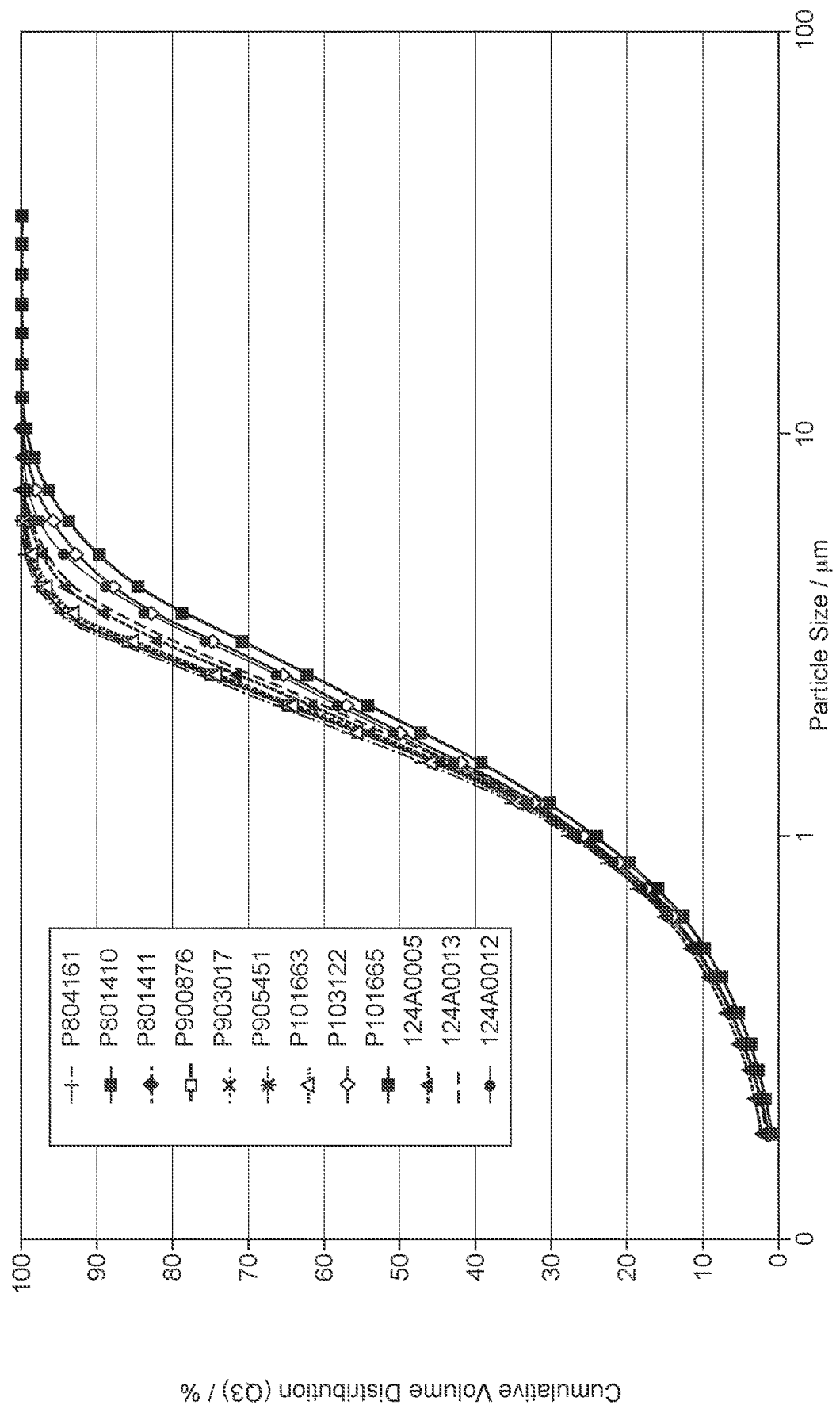
FIG. 24 shows the particle sizes of two batches of formoterol fumarate measured using a laser light scattering with a dry particle dispersion.

The particle sizes of the two batches were measured using a laser light scattering and a dry particle dispersion method, e.g. in air, such as with a Sympatec HELOS/BF equipped with a RODOS disperser and the results are set out in Table 2 and FIG. 24.

TABLE 2

Particle size of formoterol batches

| Micronisation Code | PSD | | | |
|---|---|---|---|---|
| | d10 (µm) | d50 (µm) | d90 (µm) | <10 µm (%) |
| 7544MA | 0.5 | 1.6 | 3.2 | 100 |
| | 0.6 | 1.8 | 3.4 | 100 |
| | 0.6 | 1.7 | 3.3 | 100 |
| | 0.5 | 1.6 | 3.3 | 100 |
| | 0.5 | 1.6 | 3.3 | 100 |
| | 0.5 | 1.6 | 3.4 | 100 |
| | 0.5 | 1.6 | 3.3 | 100 |
| 7544MO | 0.5 | 1.7 | 4.6 | 99 |
| | 0.5 | 1.9 | 5.1 | 99 |
| | 0.5 | 1.7 | 3.7 | 100 |
| | 0.5 | 1.7 | 3.9 | 100 |
| | 0.5 | 1.8 | 4.3 | 100 |

The particle size distribution of different batches of micronised formoterol, show an average median diameter (d50) of ca. 1.7 mm with a range of 1.6-1.9 mm. The two micronised codes, 7544MA and 7544MO, are not significantly different in fine particle size fraction, below approximately d50. However, the two micronisation codes do show clear differences in terms of their coarse particle fraction; this is clearly seen in FIG. 25. Table 2 shows that the d90 diameter for the five 7544MO formoterol batches (ca. 4.3 mm) is higher than the seven 7544MA formoterol batches (ca. 3.3 mm).

Example 2

A pharmacokinetic (PK) clinical study was conducted. The PK study assessed a number of key formulation parameters, metered dose (device dose cup volume), formulation blend strength, drug substance particle size and lactose particle size, using a stepwise approach. The PK study was carried out on the middle strength product (160/4.5 µg). Batch A contained formoterol 7544MA and batch B contained formoterol 7544MO. For both batch A and batch B, the inhaler, the budesonide and the lactose were the same.

Figure 25:
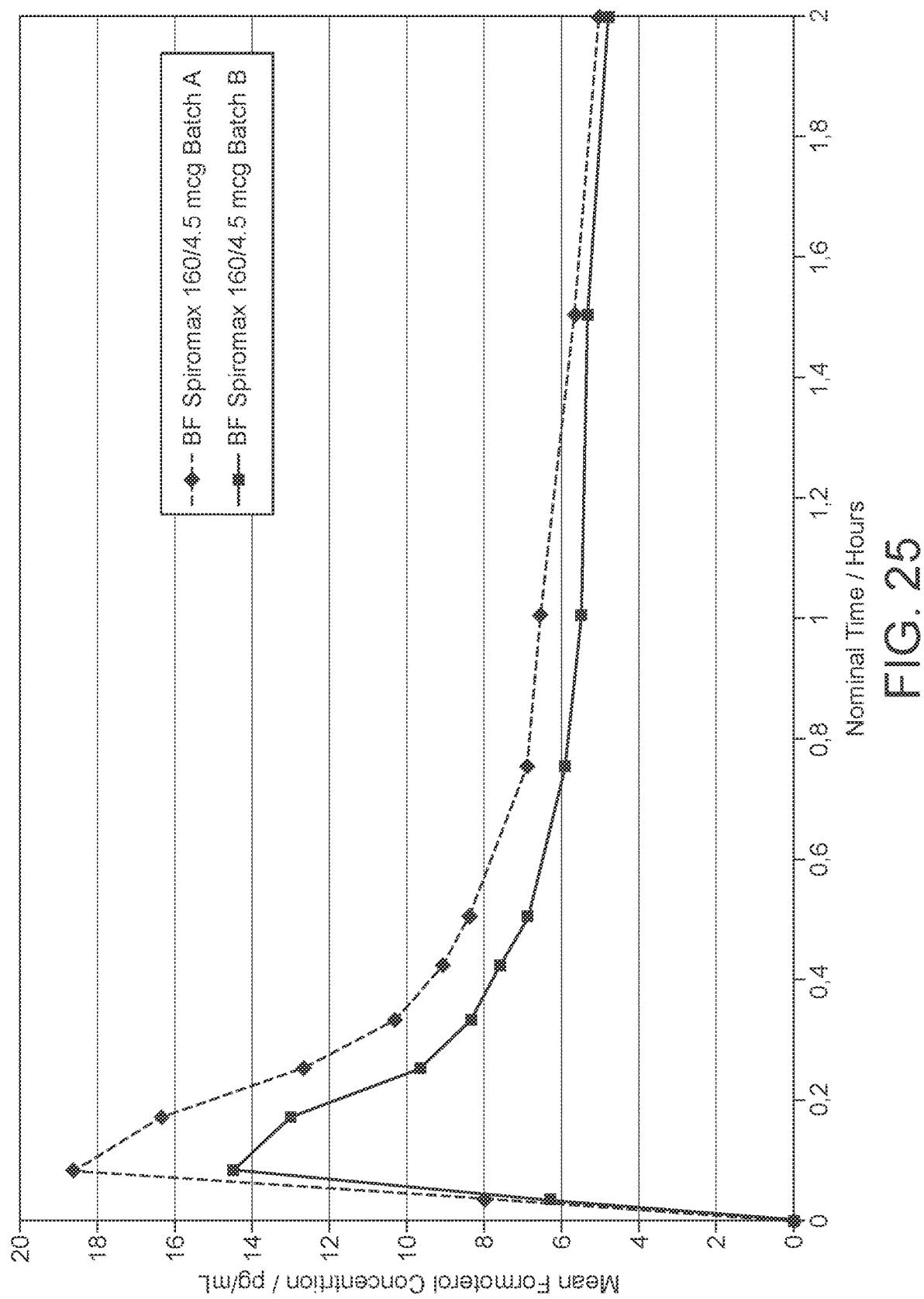
FIG. 25 shows the mean formoterol concentration over time for two batches of formoterol.

The key findings of the PK study are highlighted in FIG. 25. The data show that the coarser particle size formoterol lowers $C_{max}$ significantly, i.e. by more than 20%.

The invention claimed is:

1. A dry powder inhaler comprising:
   a reservoir containing a dry powder formulation and an arrangement for delivering a metered dose of the dry powder formulation from the reservoir; and
   a deagglomerator for breaking up agglomerates of the dry powder formulation;
   wherein active ingredients in the dry powder formulation consist of an inhalable $\beta_2$-agonist and inhalable budesonide; and
   wherein the inhalable $\beta_2$-agonist is provided in the reservoir as a micronized powder having a particle size distribution of d10<1 µm, d50=1-3 µm, d90=3.5-6 µm and NLT 99%<10 µm measured by laser diffraction as a dry dispersion.

2. The inhaler as claimed in claim 1, wherein the deagglomerator comprises:
   an inner wall defining a swirl chamber extending along an axis from a first end to a second end;
   a dry powder supply port in the first end of the swirl chamber for providing fluid communication between a delivery passageway of the inhaler and the first end of the swirl chamber;
   at least one inlet port in the inner wall of the swirl chamber adjacent to the first end of the swirl chamber providing fluid communication between a region exterior to the deagglomerator and the first end of the swirl chamber;
   an outlet port providing fluid communication between the second end of the swirl chamber and a region exterior to the deagglomerator; and
   vanes at the first end of the swirl chamber extending at least in part radially outwardly from the axis of the chamber, each of the vanes having an oblique surface facing at least in part in a direction transverse to the axis; whereby a breath-induced low pressure at the outlet port causes air flows into the swirl chamber through the dry powder supply port and the inlet port.

3. The inhaler of claim 1, wherein the reservoir is a sealed reservoir including a dispensing port, and the inhaler further comprises
   a channel communicating with the dispensing port and including a pressure relief port;
   a conduit providing fluid communication between an interior of the sealed reservoir and the pressure relief port of the channel; and
   a cup assembly movably received in the channel and including, a recess adapted to receive medicament when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

4. The inhaler of claim 1, wherein the $\beta_2$-agonist is selected from salbutamol, levosalbutamol, terbutaline, pirbuterol, procaterol, clenbuterol, metaproterenol, fenoterol, bitolterol, ritodrine, isoprenaline, formoterol, salmeterol, bambuterol, indacaterol, carmoterol, or pharmaceutically acceptable salts thereof.

5. The inhaler of claim 4, wherein the inhalable $\beta_2$-agonist is formoterol.

6. The inhaler of claim 5, wherein the formoterol is formoterol fumarate.

7. The inhaler of claim 1, wherein the formulation further comprises a lactose carrier.

8. The inhaler of claim 1, wherein the $\beta_2$-agonist has a particle size distribution of d10=0.4-0.6 µm, d50=1.5-2.5 µm and d90=3.6-5.1 µm measured by laser diffraction as a dry dispersion.

9. The inhaler of claim 8, wherein the $\beta_2$-agonist has a particle size distribution of d10=0.46-0.53 µm, d50=1.68-1.92 µm and d90=3.68-5.07 µm measured by laser diffraction as a dry dispersion.

10. A method of treating a respiratory disease in a patient comprising using the inhaler of claim 1 to administer the dry powder formulation to the patient.

11. The method of claim 10, wherein the respiratory disease is asthma or chronic obstructive pulmonary disease.

12. The method of claim 11, wherein the asthma is mild, moderate or severe asthma classed as GINA stage 1, 2, 3 or 4.

13. The inhaler of claim 1, wherein the deagglomerator is a cyclone deagglomerator.

14. The inhaler of claim 1, wherein the budesonide comprises particles less 10 µm in size.

15. The inhaler of claim 1, wherein the budesonide comprises particles with a size distribution of d10<1 µm, d50≤5 µm and d90≤10 µm measured by laser diffraction as a dry dispersion.

* * * * *